US011141606B2

(12) United States Patent
Fallone et al.

(10) Patent No.: US 11,141,606 B2
(45) Date of Patent: Oct. 12, 2021

(54) MAGNETIC RESONANCE GUIDED STEREOTACTIC RADIOSURGERY

(71) Applicant: ALBERTA HEALTH SERVICES, Edmonton (CA)

(72) Inventors: B. Gino Fallone, Edmonton (CA); Brad Murray, Sherwood Park (CA); Satyapal Rathee, Edmonton (CA)

(73) Assignee: ALBERTA HEALTH SERVICES, Edmonton (CA)

( * ) Notice: Subject to any disclaimer, the term of this patent is extended or adjusted under 35 U.S.C. 154(b) by 0 days.

(21) Appl. No.: 16/364,957

(22) Filed: Mar. 26, 2019

(65) Prior Publication Data

US 2019/0217127 A1   Jul. 18, 2019

Related U.S. Application Data

(63) Continuation-in-part of application No. PCT/CA2017/051138, filed on Sep. 26, 2017.

(60) Provisional application No. 62/399,982, filed on Sep. 26, 2016.

(51) Int. Cl.
   *A61N 5/10* (2006.01)
   *G01R 31/28* (2006.01)

(52) U.S. Cl.
   CPC ............ *A61N 5/1049* (2013.01); *A61N 5/10* (2013.01); *A61N 5/1067* (2013.01); *A61N 2005/1055* (2013.01); *A61N 2005/1061* (2013.01); *G01R 31/28* (2013.01)

(58) Field of Classification Search
   CPC ...... A61N 5/1049; A61N 5/10; A61N 5/1067; A61N 2005/1061; A61N 2005/1055; G01R 31/28
   See application file for complete search history.

(56) References Cited

U.S. PATENT DOCUMENTS

| | | | |
|---|---|---|---|
| 6,275,564 B1 * | 8/2001 | Ein-Gal | A61N 5/1049 378/65 |
| 8,958,528 B2 | 2/2015 | Fallone et al. | |
| 8,983,573 B2 | 3/2015 | Carlone et al. | |
| 2008/0009731 A1 * | 1/2008 | Maschke | A61B 8/5238 600/439 |
| 2008/0298536 A1 * | 12/2008 | Ein-Gal | A61B 6/0421 378/4 |

(Continued)

OTHER PUBLICATIONS

International Search Report and Written Opinion for Application No. PCT/CA2017/051138, dated Jan. 4, 2018.

(Continued)

*Primary Examiner* — Susan S Lee
(74) *Attorney, Agent, or Firm* — Alston & Bird LLP (57) ABSTRACT

A magnetic resonance imaging (MRI) and radiation therapy system is described. The system has a magnet gantry, an MRI apparatus, a patient support system and a radiation source head. The magnet gantry is configured to rotate about a magnet gantry axis. The MRI apparatus is coupled to the magnet gantry. The radiation source head is coupled to the MRI apparatus via a radiation source arm. The radiation source head is configured to emit a treatment beam at varying angles with respect to an azimuthal gantry axis. A method for performing stereotactic radiosurgery (SRS) using a magnetic resonance (MR)-SRS is also described.

20 Claims, 10 Drawing Sheets

(56) References Cited

U.S. PATENT DOCUMENTS

| | | | |
|---|---|---|---|
| 2009/0074140 A1* | 3/2009 | Ein-Gal | A61N 5/1049 378/65 |
| 2009/0149735 A1* | 6/2009 | Fallone | A61N 5/1049 600/411 |
| 2011/0218420 A1 | 9/2011 | Carlone et al. | |
| 2015/0190658 A1 | 7/2015 | Xinsheng | |
| 2016/0114192 A1* | 4/2016 | Lachaine | A61N 5/1038 600/1 |
| 2016/0228727 A1 | 8/2016 | Wachowicz et al. | |
| 2019/0168028 A1* | 6/2019 | Dempsey | A61N 5/1071 |

OTHER PUBLICATIONS

Baldwin, L. N., et al., "A two-step scheme for distortion rectification of magnetic resonance images", Medical Physics, Sep. 2009, pp. 3917-3926, vol. 36, No. 9, Wiley Periodicals, Inc., US.

Baldwin, L. N., et al., "Characterization, prediction, and correction of geometric distortion in 3 T Mr images", Medical Physics, Feb. 2007, pp. 388-399, vol. 34, No. 2, Wiley Periodicals, Inc., US.

Crooks, Ian A., et al., "A CT- and MR-compatible reference marker box for use with stereotaxtic frames", American Journal of Roentgenology, Jan. 1995, pp. 178-180, vol. 164, American Roentgen Ray Society, US.

Hristov, D.H., et al., "A grey-level image alignment algorithm for registration of portal images and digitally reconstructed radiographs", Medical Physics, Jan. 1996, pp. 75-84, vol. 23, No. 1, Wiley Periodicals, Inc., US.

Keyvanloo, A., et al., "Minimal skin dose increase in longitudinal rotating biplanar linac-MR systems: examination of radiation energy and flattening filter design", Physics in Medicine and Biology, Apr. 2016, pp. 3527-3539, vol. 61, IOP Publishing, UK. (Retracted Apr. 2, 2020 Phys. Med. Bio., vol. 65, IOP Publishing, UK).

Keyvanloo, A., et al., "Skin dose in longitudinal and transverse linac-MRIs using Monte-Carlo and realistic 3D MRI field models", Medical Physics, Oct. 2012, pp. 6509-6521, vol. 39, No. 10, Wiley Periodicals, Inc., US.

Kirkby, C., et al., "Lung dosimetry in a linac-MRI radiotherapy unit with a longitudinal magnetic field", Medical Physics, Sep. 2010, pp. 4722-4732, vol. 37, No. 9, Wiley Periodicals, Inc., US.

Kirkby, C., et al., "Magnetic field effects on the energy deposition spectra of MV photon radiation", Jan. 2009, Physics in Medicine and Biology, pp. 243-257, vol. 54, No. 2, IOP Publishing, UK.

Kirkby, C., et al., "Patient dosimetry for hybrid MRI-radiotherapy systems", Medical Physics, Mar. 2008, pp. 1019-1027, vol. 35, No. 3, Wiley Periodicals, Inc., US.

Otto K., et al., "Frame slippage verification in stereotactic radiosurgery", International Journal of Radiation Oncology Biology Physics, Apr. 1998, pp. 199-205, vol. 41, No. 1, Elsevier Science, Inc., Netherlands.

Sirois, L. M., et al., "Three-dimensional anatomy setup verification by correlation of orthogonal portal images and digitally reconstructed radiographs", Medical Physics, Nov. 1999, pp. 2422-2428, vol. 26, No. 11, Wiley Periodicals, Inc., US.

St. Aubin, J., et al., "A deterministic solution to the first order linear Boltzmann transport equation in the presence of external magnetic fields", Medical Physics, Feb. 2015, pp. 780-793, vol. 42, No. 2, Wiley Periodicals, Inc., US.

St. Aubin, J., et al., "Discontinuous finite element space-angle treatment of the first order linear Boltzmann transport equation with magnetic fields: Application to MRI-guided radiotherapy", Medical Physics, Jan. 2016, pp. 195-204, vol. 43, No. 1, Wiley Periodicals, Inc., US.

Stanescu, T., et al., "A study on the magnetic resonance imaging (MRI)-based radiation treatment planning of intracranial lesions", Physics in Medicine and Biology, Jun. 2008, pp. 3579-3593, vol. 53, No. 13, IOP Publishing, UK.

\* cited by examiner

MAGNETIC RESONANCE GUIDED STEREOTACTIC RADIOSURGERY

CROSS-REFERENCE TO RELATED APPLICATIONS

This application is a continuation-in-part of International Application No. PCT/CA2017/051138, filed Sep. 26, 2017, which claims priority to and the benefit of U.S. Provisional Patent Application No. 62/399,982, filed Sep. 26, 2016, each of which is hereby incorporated by reference in its entirety.

FIELD

The present invention relates generally to Magnetic Resonance Imaging (MRI) and specifically to a system and method configured to facilitate Magnetic Resonance Guided Stereotactic RadioSurgery (MR-SRS).

BACKGROUND

Work has been ongoing on the development of an integrated linear accelerator—magnetic resonance imaging MRI device (Linac-MR) for real-time image guided radiotherapy purposes.

Stereotactic Radiosurgery has been used for several decades to treat various neurological disorders such as brain metastasis, solitary primary brain tumors, arteriovenous malformations (AVM), pituitary adenoma and acoustic neuroma. It has more recently been used to treat some functional disorders such as Parkinson's disease.

Current Stereotactic Radiosurgery devices consist of customized linear accelerators, such as devices provided by BrainLab AG and Accuray Incorporated, or devices using 201 Cobalt sources, such as devices provided Elekta Ltd. These devices are used to deliver very high radiation dose to ablate the tumor/lesion in a single treatment, or a small number of daily treatments. Intended lesions are often situated in close proximity to the other functionally sensitive areas of the cranium. Thus, a very high geometric accuracy in aligning the target volume encompassing the lesion(s) is needed to ensure that the radiation is delivered substantially to the lesion(s) and negligibly everywhere else.

Although MRI, computed tomography (CT), and angiography are commonly used for pre-planning localization of intended lesions and treatment planning, the imaging of patient on radiation delivery systems is typically limited to two or more 2D radiographs. Thus, a direct visualization of lesions immediately before and during the radiation delivery is typically not possible. Because of this limitation, invasive frames are often attached to the skull to ensure that the patient is set up accurately on the treatment machine. The invasive frame is attached to the patient prior to the multiple treatment planning imaging studies mentioned above and remains affixed to the patient for several hours during the day or even for the whole day. The frame defines a common geometric reference, or more accurately a coordinate system, for all the imaging systems and subsequently for the radiation beam delivery system. This requires placement and replacement of surrogate markers particularly visible to each imaging system including those on the beam delivery system such that the lesion is aligned to the radiation beam as per the treatment plans. See, for example, I. A. Crooks, B. G. Fallone, E. B. Podgorsak and N. Sharoubim, "A CT- and MR-compatible fiducial marker box for use with stereotactic frames", American Journal of Roentgenology, 164, pp. 178-180, 1995, where the same stereotactic frame can be used as the marker for MR, for CT and for 2D radiographs.

Substantial work has been done to provide frameless radiosurgery to allow a less traumatic experience for the patient. See, for example, D. H. Hristov and B. G. Fallone, "A grey-level image alignment algorithm for registration of portal images and digitally reconstructed radiographs", Med. Phys., 23, pp. 75-84, 1996; K. Otto and B. G. Fallone, "Frame slippage verification in stereotactic radiosurgery", It. J. Rad. One. Biol. Phys., 41(1), pp. 199-205, 1998; and L. Sirois, D. Hristov and B. G. Fallone, "3-D anatomy set up verification by correlation orthogonal portal images and DRRs", Med. Phys., 26(11), pp. 2422-2428, 1999. These techniques rely on CT or X-ray-based imaging techniques which allow for good visualization of bony structures, but poor visualization of soft tissue. This is a significant weakness in these techniques. Because of poor visualization of soft-tissue lesion and the nearby sensitive areas of brain, invasive frames are often used to improve confidence in treatment delivery.

SUMMARY

In accordance with an aspect of an embodiment, there is provided a magnetic resonance imaging (MRI) and radiation therapy system, the system comprising: a magnet gantry configured to rotate about a magnet gantry axis, an MRI apparatus coupled to the magnet gantry; a patient support system; and a radiation source head coupled to the bi-planar MRI apparatus via a radiation source arm; wherein the radiation source head is configured to emit a treatment beam at varying angles with respect to an azimuthal gantry axis.

In accordance with another aspect of an embodiment, there is provided a method for performing stereotactic radiosurgery (SRS) using a magnetic resonance (MR)-SRS system, the method comprising: generating a treatment plan in accordance with at least one acquired MR image of a target; treating the target using a radiotherapy treatment beam of the MR-SRS system based on the treatment plan; acquiring further MR images simultaneously to the treating the target to detect motion of the target; and modifying the treating the target to correct for the motion of the target.

In accordance with another aspect of an embodiment, there is provided a magnetic resonance imaging (MRI) and radiation therapy system, the system comprising: an MRI apparatus configured to rotate about a magnet gantry axis, a patient support system; and a radiation source head configured to emit a treatment beam at varying angles with respect to an azimuthal gantry axis.

BRIEF DESCRIPTION OF THE DRAWINGS

Embodiments of the invention will now be described by way of example only with reference to the following drawings in which.

DETAILED DESCRIPTION OF THE PREFERRED EMBODIMENTS

Figure 1:
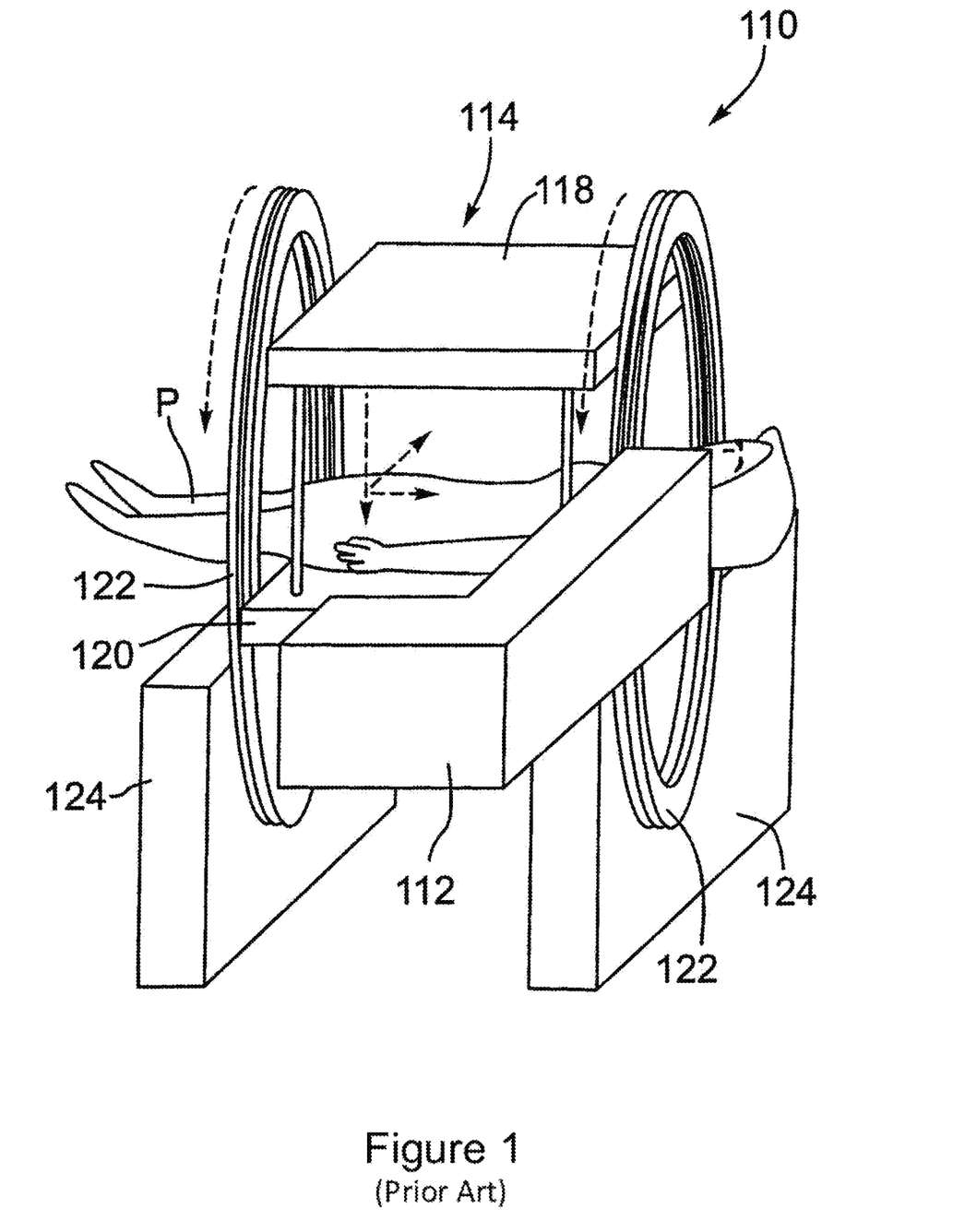
FIGS. 1 to 3 are illustrations of a combined MRI and radiation source apparatus (prior art)
Figure 2:
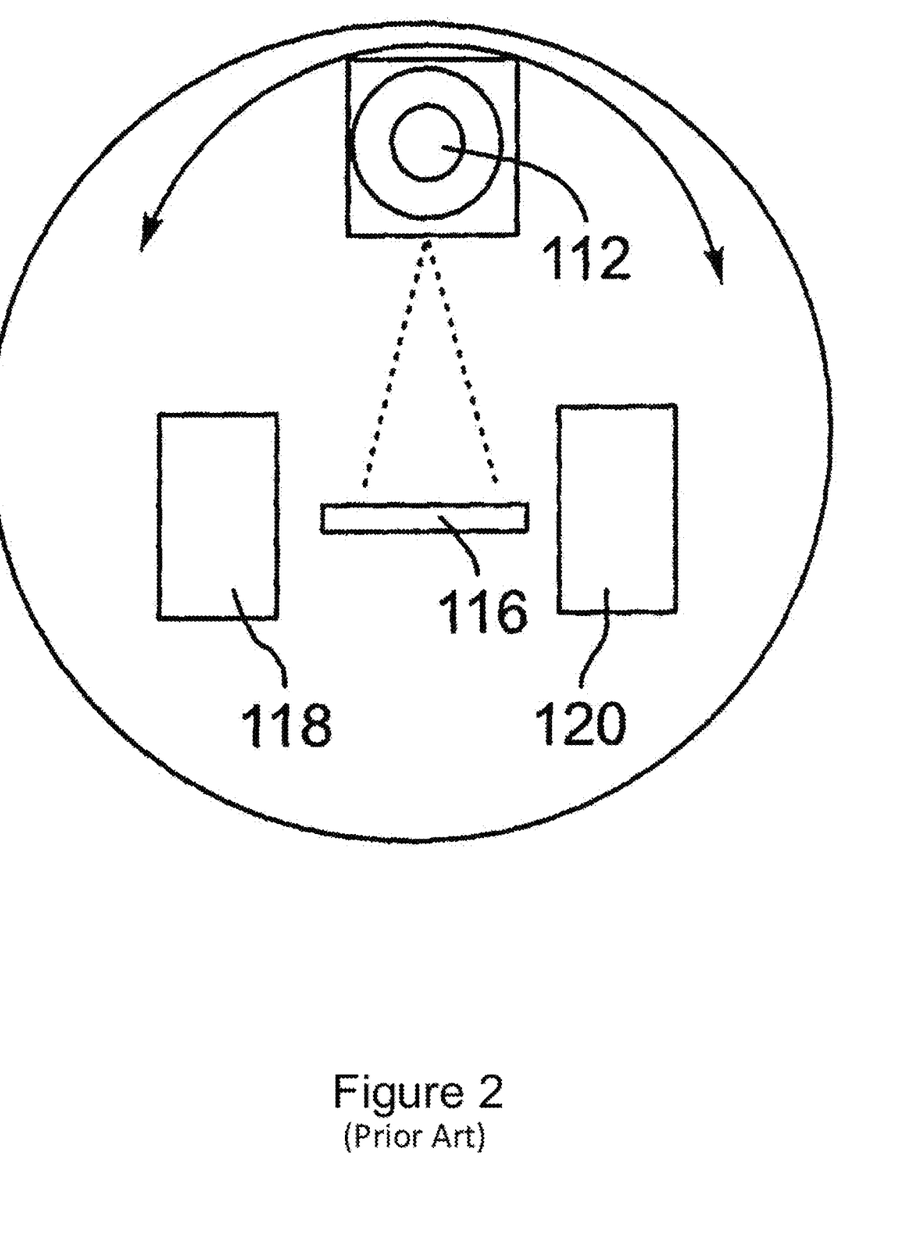
Figure 3:
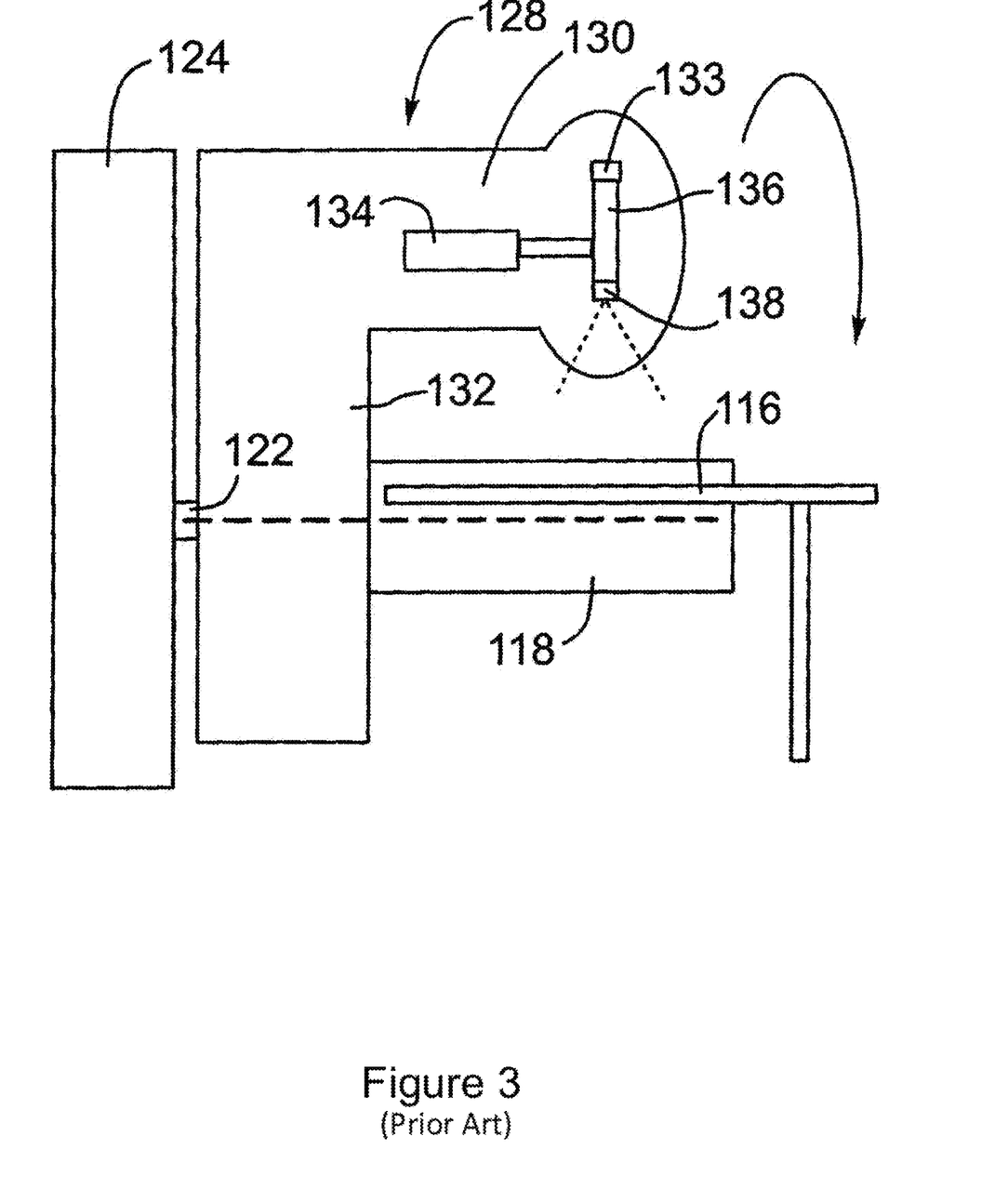

For convenience, like numerals in the description refer to like structures in the drawings. Referring to FIGS. 1 to 3, an integrated radiation source and MRI system is shown and is generally identified by reference numeral 110. As can be seen, the integrated radiation source and MRI system 110 includes a radiation source and an MRI apparatus 114. In an embodiment, the radiation source is a linear accelerator or linac 112. As will be described, the radiation source 112 is configured to generate a treatment beam. The MRI apparatus 114 is configured to image a patient in real-time. The radiation source 112 and the MRI apparatus 114 are coupled to a rotatable magnet gantry 122 so that they can be rotated in unison to treat a patient P.

In this particular example, the MRI apparatus 114 comprises a bi-planar magnet having a pair of opposing magnet poles 118 and 120 creating a 0.5T magnetic field strength, although other field strengths may be used. The MRI apparatus 114 is an open bore type including a patient support system (couch) 116 on which the patient P can lay. In FIG. 1, the magnet poles 118 and 120 of the bi-planar magnet are disposed above and below the couch 116. The radiation source 112 and magnet poles 118 and 120 are mounted on the magnet gantry 122 that is supported by a frame 124. In FIG. 2, the magnet gantry 122 is rotated, and the magnet poles 118 and 120 of the bi-planar magnet are disposed on the left-hand side and right-hand side of the couch 116, respectively.

The linac 112 includes a head 128 housing an electron beam generator 130 mounted on an arm 132 that is affixed to the magnet gantry 122. In this manner, the linac 112 rotates in unison with the magnet gantry 122 and thus, maintains its position relative to the magnet poles 118 and 120. If desired, the linac 112 may have its own gantry. In this case, the gantry of the linac 112 and the magnet gantry 122 are mechanically coupled so that the linac 112 rotates in unison with the magnet poles 118 and 120.

The electron beam generator 130 includes an electron gun 133, an RF generator 134, an accelerating waveguide 136, a heavy metal target 138 at one end of the accelerating waveguide 136 and a beam collimating device (not shown). Interference reducing structure is also provided to inhibit the linac 112 and MRI apparatus 114 from interfering with one another during operation.

Alternatively, the linac 112 and MRI apparatus 114 may be mechanically coupled so that the electron beam is directed horizontally, and the magnet poles 118 and 120 are mounted vertically such that the magnetic field is horizontal, but perpendicular to the electron beam. These two components are fixed and non-movable. Variable angle electron or photon beam delivery is allowed by rotating the subject while in a sitting position. This integrated linac and MRI system configuration is particularly useful for lung cancer subjects who prefer standing/seating to laying supine, and for whom, conventional CT simulation does not allow simulation in the sitting position.

Further specifics of the integrated radiation source and MRI system 110 are described in U.S. Pat. Nos. 8,958,528 and 8,983,573, the contents of which are incorporated by reference. Additionally, other systems designed to integrate a radiation source with an MRI system may also be employed.

Although these systems are capable of Stereotactic Radiation Therapy (SRS) treatment, it is necessary to reduce the radiation delivered to normal brain tissue during SRS. Similarly, although these systems are capable of Stereotactic Body Radiation Therapy (SBRT) treatment, it is desirable to reduce the radiation delivered to normal tissue during SBRT. Accordingly, referring to FIG. 4, system configure to facilitate a magnetic resonance guided stereotactic radiosurgery (MR-SRS) system in accordance with an aspect of an embodiment is illustrated generally by numeral 400. Similarly to the system illustrated in FIGS. 1 to 3, the MR-SRS system 400 comprises an MRI apparatus 114 and a radiation source 112. The MRI apparatus 114 comprises a bi-planar magnet having a pair of spaced apart magnetic poles 118 and 120. In the illustrated embodiment, the bi-planar magnet is C-shaped and the magnetic poles 118 and 120 are connected at one end by a substantially perpendicular coupling plate 402.

Figure 4A:
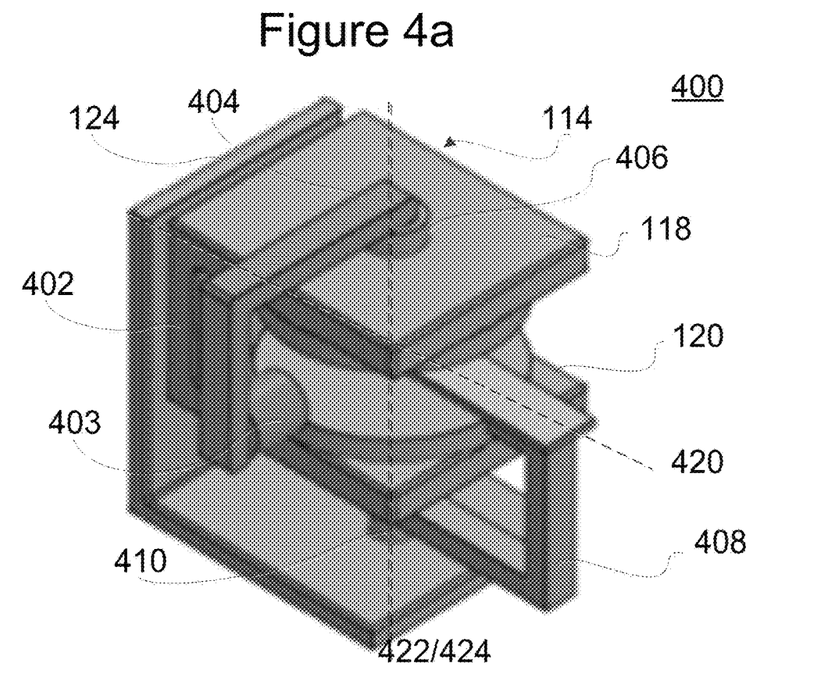
FIG. 4a illustrates the combined MRI and radiation source apparatus in accordance with an embodiment.
Figure 4B:
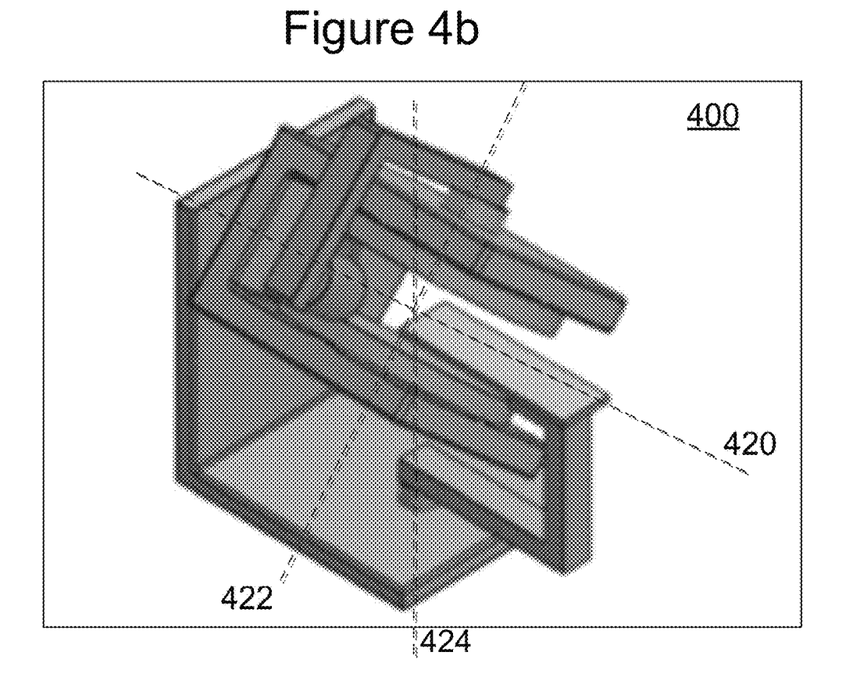
FIG. 4b illustrates rotation of MR apparatus about a magnet gantry axis.

The bi-planar magnet is mounted on the magnet gantry 122, which is rotationally coupled to the frame 124. The magnet gantry 122 is configured to rotate about a magnet gantry axis 420. As will be appreciated, the magnet gantry axis 420 is fixed with respect to the frame, since the frame 124 does not move. The magnet gantry axis 420 is substantially parallel to the long axis of the patient P. Thus, the bi-planar magnet has one rotational degree of freedom The radiation source head 403 is coupled to a source arm 404, which is in turn coupled to an azimuthal gantry 406. In an embodiment, the radiation source 112 is mounted to the radiation source head 403. The azimuthal gantry 406 is rotationally coupled with one of the pair of spaced apart magnetic poles 118 and 120. Accordingly, the azimuthal gantry 406 is configured to rotate about an azimuthal gantry axis 422. The source arm 404 is C-shaped to allow the radiation source 112 to rotate about the patient P in a plane substantially parallel to the magnetic poles 118 and 120, referred to as the azimuthal plane. The azimuthal gantry axis 422 is fixed with respect to the magnet gantry axis 420, by virtue of its coupling to the bi-planar magnet. However, the azimuthal gantry axis 422 moves with respect to the frame 124 as the bi-planar magnet rotates about the magnet gantry axis 420. Thus, the radiation source 112 has two rotational degrees of freedom. In the present embodiment, rotation of the azimuthal gantry 406 about the azimuthal gantry axis 422 is restricted to avoid impact between the radiation source 112 and the frame 124. Alternatively, the accelerator arm 404 is configured to avoid contact with the frame 124, and the rotation of the azimuthal gantry 406 about the azimuthal gantry axis 422 is unrestricted. Alternatively, the azimuthal gantry 406 can be limited to a restricted angle of rotation of approximately 20 or 30 degrees about the azimuthal gantry axis 422 in the azimuthal plane. Even such a restricted angle of rotation will likely be enough to ensure the beam path does not have significant overlap as the magnet gantry rotates. Different angular limits could be used depending on the implementation of the system 400. In an embodiment, the azimuthal plane is orthogonal to a plane in which the magnet gantry rotates.

Figure 6A:
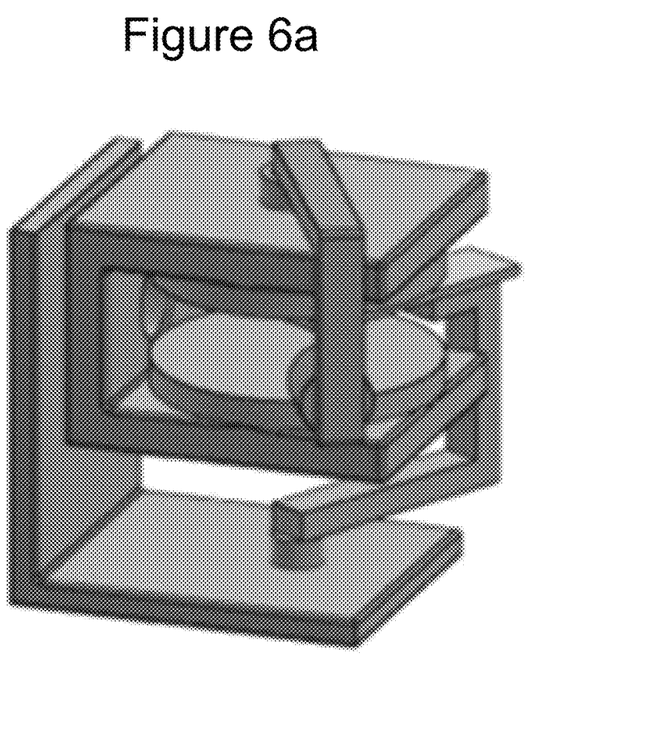
FIGS. 6a and 6b illustrate rotation of a patient support system about a couch gantry axis.
Figure 6B:
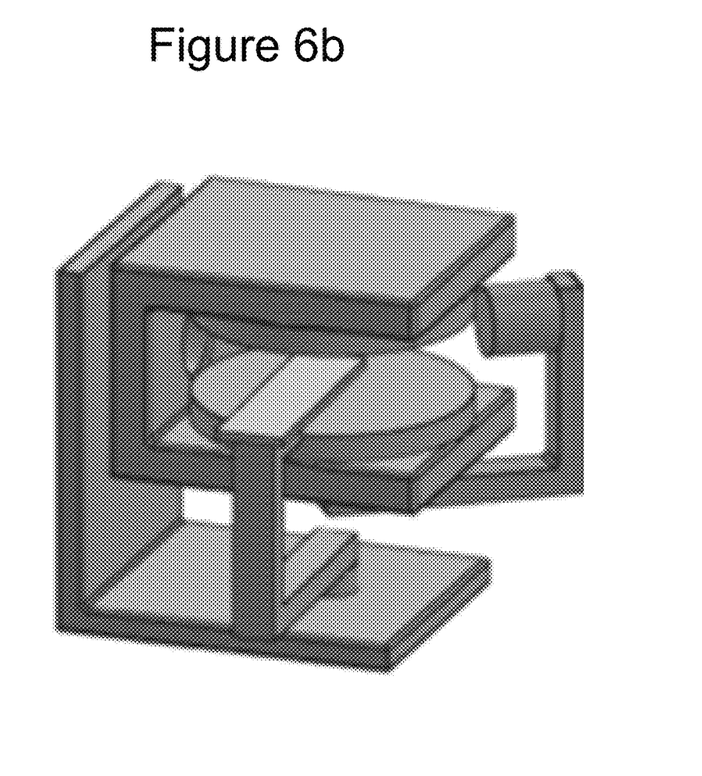

In an embodiment, the couch 116 is coupled to a couch arm 408, which is in turn coupled to a couch gantry 410. The couch gantry 410 is rotationally coupled with the frame 124 or the floor. Accordingly, the couch gantry 410 is configured to rotate about a couch gantry axis 424. The couch arm 408 is C-shaped to allow the couch to rotate the patient P in a plane substantially parallel to the magnetic poles 118 and 120. The couch gantry axis 424 is fixed by virtue of its coupling to the frame 124 or floor. The couch gantry axis 424 is substantially perpendicular to the long axis of the patient P (parallel to the transverse axis of the patient P). When used in combination with the magnet gantry 122 and the azimuthal gantry 406, the couch gantry 410 provides an additional rotational degree of freedom. Further, in an embodiment, the couch is capable of being translated as described in U.S. Patent Application Publication No. 2016/0228727.

The multiple degrees of rotation facilitates gantry arc irradiation at multiple angles of the couch 116, thus providing treatment from multiple, non-coplanar planes. This inhibits the likelihood of entrance and exit beams from any two arcs coinciding.

The magnet gantry axis 420, the azimuthal gantry axis 422, and the couch gantry axis 424 intersect at a point in space referred to as the isocentre. As the magnet gantry rotates in the axial plane, the plane of the azimuthal axis would become tipped from the vertical. Thus, between the two rotations, radiation could be delivered from numerous non-coplanar directions. Consider an example in which the azimuthal gantry is rotated by a fixed angle. Then, if the radiation is delivered while rotating the magnet gantry, it would create a conical radiation path aimed at the isocentre.

Figure 5A:
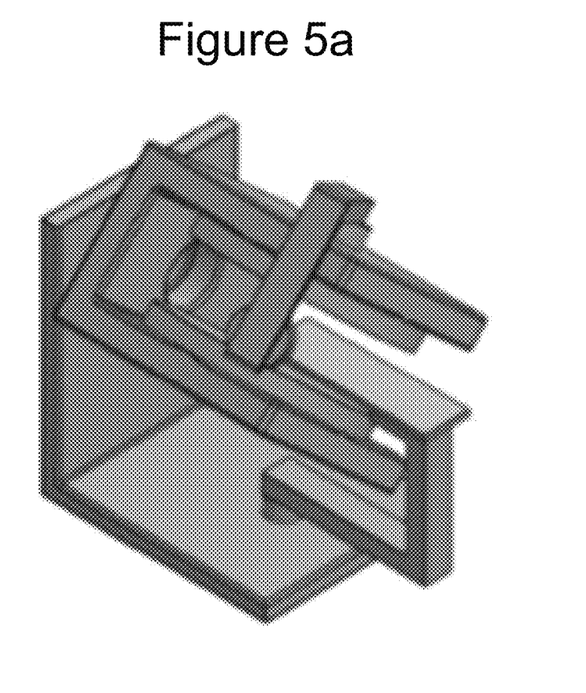
FIGS. 5a and 5b illustrate rotation of a radiation source about a source gantry axis.
Figure 5B:
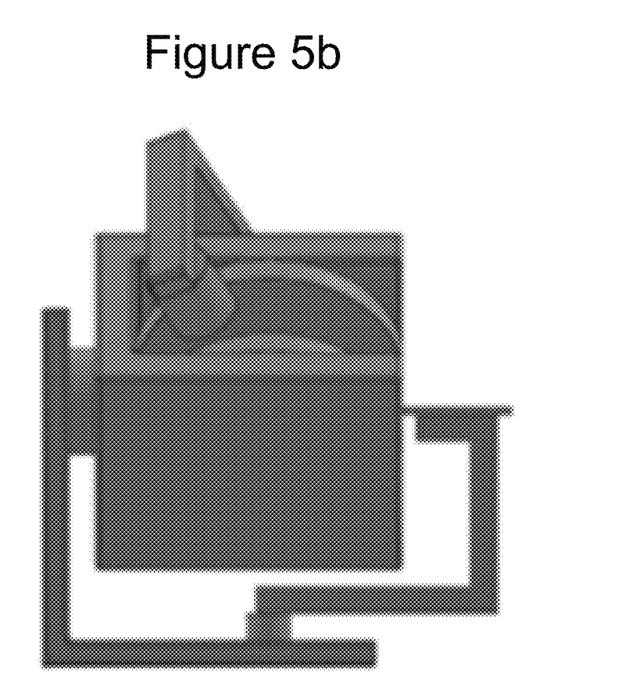

The MR-SRS system 400 has the ability to move both the azimuthal and magnet gantries independently of each other. This enables delivery from: several stationary beams; several arcs of the magnet gantry with the azimuthal gantry at a different location for each arc; several arcs of the azimuthal gantry with the magnet gantry at a different location for each arc; and/or a combined arc moving both gantries simultaneously. For example, FIGS. 5a and 5b show motion of the azimuthal gantry and motion of the magnet gantry. The motion of the azimuthal gantry is independent of the motion of the magnet gantry. Specifically, FIG. 5(a) shows the radiation source 112 directed from an inferior direction to the isocentre. FIG. 5(b) shows the radiation source 112 directed from a superior direction through isocentre. The magnet gantry may be oriented to any angle with any azimuthal gantry angle, or the two may be arced independently.

Additionally, with the magnet gantry at 90 degrees (in which the magnet poles are substantially horizontal), both the couch gantry and azimuthal gantry could be rotated independently thus allowing treatment from numerous treatment angles in the coronal plane. This could be accomplished through arc rotations of the couch gantry and/or azimuthal gantry, or through several stationary fields at different couch gantry and azimuthal gantry locations. For example, FIGS. 6a and 6b show motion of the couch gantry and motion of the azimuthal gantry. The motion of the azimuthal gantry is independent of the motion of the couch gantry. Specifically, FIG. 6(a) shows the radiation source 112 on the patient's right. The couch may be rotated 90° or more to the patient's left allowing the any beam angle in the coronal plane up to a superior beam. FIG. 6(b) shows the radiation source 112 on the patient's left, illustrating that the complimentary angles on the patient's right may be treated.

Thus, a combination of couch rotation and radiation source rotation can be used to treat the upper hemisphere of the patient in the coronal plane.

As will be appreciated, the separation of the faces of the magnet poles 118 and 120 is large enough to allow the bi-planar magnet to rotate freely around a typical patient torso. For example, this distance is approximately 55 cm or larger. For a cranial SRS machine, the separation of the faces of the magnet poles 118 and 120 is optimized to ensure that the magnet can rotate freely around the head of any patient. For example, this distance is approximately 35 cm.

The magnet homogeneity is optimized to provide high quality imaging over the entire treatment area. As an example, a typical treatment are for SBRT is approximately 35 cm and for SRS is approximately 20 cm. Any field strength could be used. However, the field strength is a compromise between the optimum imaging characteristics, the dose perturbation caused by the magnetic field and magnetic and radiofrequency (RF) shielding design issues. It is expected that a field strength between 0.5T-1.5 T would be optimum, however, other field strengths are possible. Further, a wide variety of magnet sizes may be used to allow the system to be optimized for a given body region.

Imaging sequences provide high quality images of brain tumors, as well as MR angiography for defining AVM locations. Functional imaging to determine areas to be treated for neurological disorders could also be incorporated. As described in U.S. Pat. No. 8,983,573, if the radiation source 112 and MRI apparatus 114 rotate in unison, then the radiation source is stationary with respect to the MRI apparatus. Thus, minimal image distortions are be caused by rotation.

However, in the present system described, rotation of the azimuthal gantry 406 causes the radiation source 112 to move relative to the MRI apparatus 114. Accordingly, additional active and passive shimming may be required to compensate for distortions that may be caused by this motion. Properly designed systems with minimal use of ferromagnetic material minimize the distortion caused by this motion. Accordingly, in an embodiment, the azimuthal gantry 406 and the couch gantry 410 are constructed from non-magnetic materials, such as non-magnetic stainless steel, or non-magnetic alloys of aluminum. One of ordinary skill in the art will appreciate that other materials with non-magnetic properties may be used, such as plastics, titanium and the like. In order to minimize the effect and need for active shimming, a main MRI shim is determined with the azimuthal gantry 406 at a fixed position. In an embodiment, the fixed position is at 0 degrees, but it could be at other positions.

In an alternative embodiment, a four post bi-planar magnet is used instead of the C-shaped bi-planar magnet disclosed above. However, using a biplanar magnet that is supported by four posts would yield two exclusion areas in which the radiation would be attenuated by the posts. Accordingly, the MR-SRS system is designed to ensure that no radiation would be delivered from these angles. This limitation does not significantly impact performance of the MR-SRS system, as there is sufficient flexibility to bring the radiation in from many angles without significantly affecting the dose distribution produced.

Figure 11:
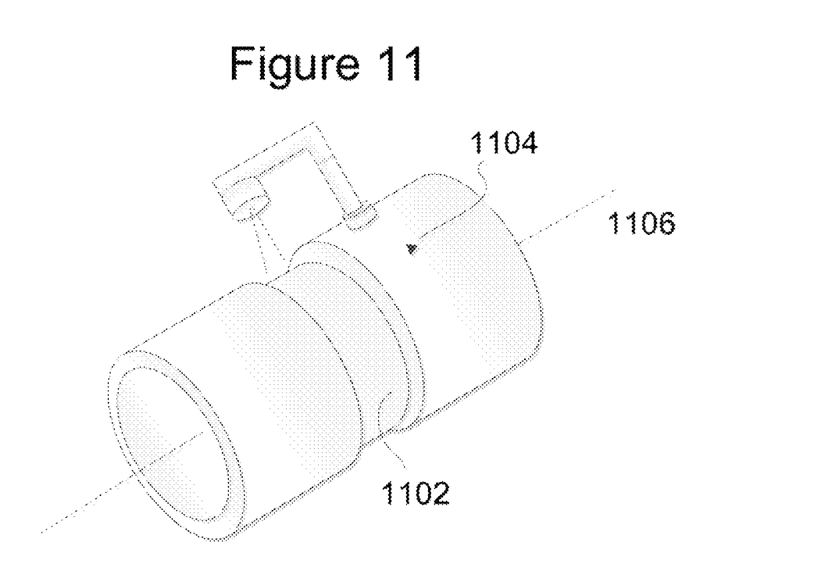
FIG. 11 illustrates an embodiment in which the MR apparatus is cylindrical.

In an alternative embodiment, a cylindrical magnet, as illustrated in FIG. 11, is used instead of the C-shaped bi-planar magnet disclosed above. In this embodiment it is possible to create a portion 1102 of the cylindrical magnet 1104 that has minimal or no radiation attenuating materials that would perturb the beam path of the treatment. By rotating the cylindrical magnet about its axis 1106 the area that has radiation penetration is constant. Those experienced in the art will recognize that a Helmholtz or a split cylindrical magnet can also be used instead of the standard cylindrical magnet disclosed above.

In an alternative embodiment, the patient is seated on a chair instead of lying on the couch. In this embodiment the MR-SRS system is mounted above the floor with a substantial vertical magnet gantry axis. Such a configuration aligns with the axial plane of the patient, thereby keeping a similar orientation between the patient P and magnet assembly to the embodiment described above. In this embodiment, the chair has a mechanical lift mechanism to appropriately position the patient relative to the treatment beam.

Alternatively, the seated configuration described above can be implemented using a fixed bi-planar magnet. Instead of rotating the magnet, the chair is rotated to any position in the axial plane. The azimuthal rotation is achieved by rotating the particle source in the coronal plane, such that between the two rotations, radiation can be brought in from substantially any angle in the superior hemisphere.

Alternatively, rather than being seated, the patient support system is used to immobilize the patient in another position, such as standing for example.

In an alternative embodiment, an x-ray detector is mounted on a side of the patient opposite to the radiation source. The x-ray detector is capable of measuring the beam intensity received thereat. Thus, by rotating the magnet gantry the system can measure the intensities received at the x-ray detector for each angle in order to reconstruct a CT image of the patient. The CT image can be co-registered with the MR images for better visualization of bony anatomy. The CT image may also be used for modeling the heterogeneity effects in the dose calculation.

In the embodiments described above, it is foreseen that any radiation source could be used. For example, the radiation source may provide photons, such as gamma rays and X-rays, charged particles, such as electrons, protons, and ions, or neutrons.

Figure 10:
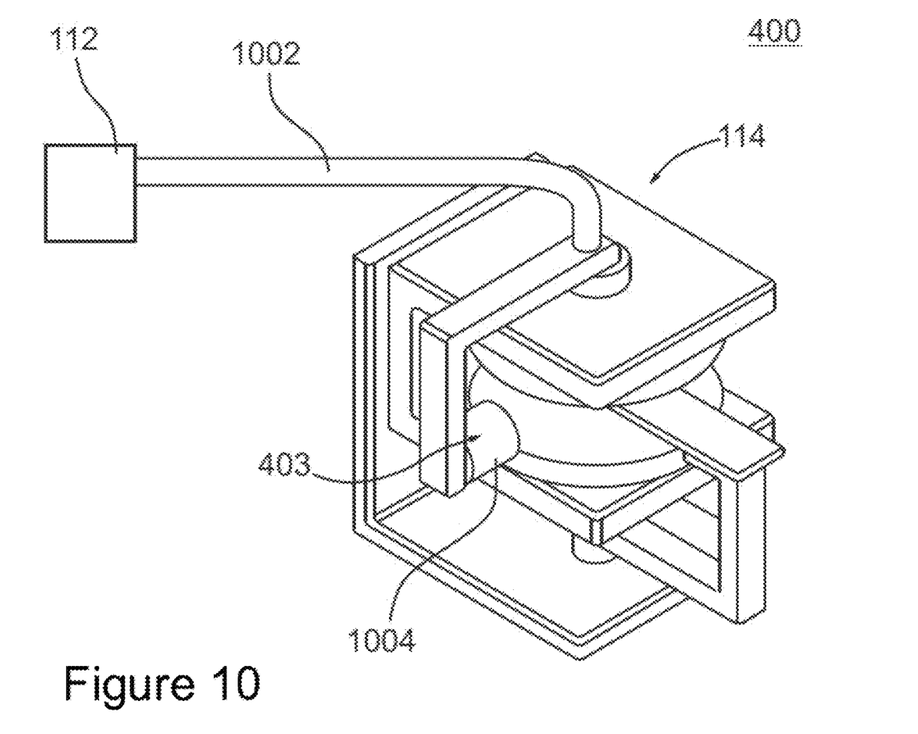
FIG. 10 illustrates the MRI apparatus in which the radiation source is remote from the MRI.

In the embodiments described above, the radiation source 112 itself is mounted to the radiation source head 403 of the MR-SRS system 404. In an alternative embodiment, the radiation source 112 may be remote from the MR-SRS system 400, as illustrated in FIG. 10. In such an embodiment, a treatment beam of charged particles, such as electrons, protons, carbon ions, and the like, can be transported from the remote radiation source 112 to the radiation source head 403 using a beam transport device. In an embodiment, the beam transport device includes waveguides 1002 to guide the beam and bending magnets 1004 to redirect the beam from travelling in a straight line. In such an embodiment, allowing the source arm 404 to rotate about the azimuthal gantry 406 may not be possible. Accordingly, rather than rotate the source arm 404, variations in the angle of the treatment beam can be achieved by varying the currents to the bending magnets 1004. Specifically, the bending magnets 1004 placed at and near a point at which the beam exits the beam transport device at the radiation source head 403 can be manipulated to change the direction of the beams as it exits. Such variation will cause the treatment beam to exit the radiation source 403 in a variety of different, controllable angles in the azimuthal plan. Although the variety of different angles in the treatment beam may not be as great as in the embodiment in which the radiation source 112 is rotated about the azimuthal axis, it is anticipated that the variety of different angles available in the present embodiment will be sufficient to be effective.

In an alternative embodiment, the MRI apparatus is mounted on rails and configured such that it may be moved into place over the patient. The patient is imaged and positioned accurately. The MRI apparatus is then removed from the patient area and the treatment may be delivered using any conventional radiotherapy system.

In an alternative embodiment, the particle source may be mounted independently from the MRI apparatus. The particle source can be manipulated using robotic arms to deliver a radiation beam from a plurality of different locations. The MRI apparatus may still need to rotate in order to create a beam path without interference from intervening materials at certain desired beam angles.

Using the MR-SRS system 400 described above, a clinician will be able to see a target image while treating the patient, thus providing the confidence to treat the patient without requiring the frame.

Further, using the MR-SRS system, treatments may have great benefit since the lesion as well as nearby sensitive areas of brain would be visible on the pre-treatment imaging available on the MRI apparatus. Thus, the target volume containing the lesion is easily and confidently aligned pre-treatment and during treatment with the coordinate system of the MR-SRS system. Thus, the invasive stereotactic frame would not be required. Having this capability may also eliminate some or all of the imaging required for planning, as one could imagine all planning and delivery being done in a single session based on the pre-treatment image taken on the MR-SRS system. Since the MR images show the target, there is no need to use other modalities and fuse the images. Therefore, it is possible that the entire procedure may be done in a single session utilizing this single device.

Although the MR-SRS system was designed specifically for SRS, its benefits are not limited to SRS. Stereotactic Body Radiotherapy (SBRT) is commonly used for extracranial lesions. For SBRT, MR guidance may also be useful. Unlike SRS, it is often not feasible to use couch rotations of more than a few degrees due to the potential for collisions between the gantry and the patient with the source arm. In many cases SBRT is limited to coplanar treatment fields due to these potential collisions. Therefore adding the ability to use MR-Guided radiotherapy for SBRT and enabling non-coplanar treatment angles may be beneficial. Yet further, the MR-SRS system may be used for radiotherapy for any appropriate body/tumor location and any number of fractions.

Although it would be feasible to use a conventional approach to treatment planning process for the MR-SRS system, a more integrated approach is desirable. An integrated treatment planning system comprises modifications to the imaging system to incorporate treatment planning functionality designed specifically for the MR-SRS system described. The treatment planning system has the ability to model rotations of both the magnet gantry and the radiation source gantry. The treatment planning system also has to take into account exclusion zones to prevent radiation from being delivered through any structures, such as support posts, that would attenuate the beam in an undesirable way. The treatment planning system includes image distortion correction routines to ensure geometric accuracy of the planning images. Examples of such image distortion correction routines are described by L. N. Baldwin, K. Wachowicz, S. D. Thomas, R. Rivest and B. G. Fallone, "Characterization, Prediction, and Correction of Geometric Distortion in 3 T MR Images", Med. Phys. 34(2), pp. 388-399 (2007), L. N. Baldwin, K. Wachowicz, B. G.

Fallone, "A two step scheme for distortion rectification of magnetic resonance images", Medical Physics 36(9), pp. 3917-3926 (2009); and T. Stanescu, J-S Jans, N. Pervez, B. G. Fallone, "A study on the MRI-based radiation treatment planning of intracranial lesions", Phys Med Biol, 53(13), 3579-3593 (2008). The treatment planning system displays functional and anatomical data overlaid on the image, such that the functional image could be used in the design of the beam delivery. The treatment planning also has all conventional capabilities of radiation therapy and radiosurgery planning systems.

Dose calculations that incorporate the effects of magnetic fields can be calculated using Monte Carlo methods as described by C. Kirkby, T. Stanescu, S. Rathee, M. Carlone, B. Murray, and B. G. Fallone. "Patient dosimetry for hybrid MRI-radiotherapy systems", Med Phys, 35(3), pp. 1019-1027 (2008), C. Kirkby, T. Stanescu, B. G. Fallone, "Magnetic field effects on the energy deposition spectra of MV photon radiation", Phys Med Biol, 54(2), 243-257 (2009), C. Kirkby, B. Murray, S. Rathee, B. G. Fallone, "Lung dosimetry in a linac-MR radiotherapy unit with a longitudinal magnetic field", Medical Physics, 37(9) pp. 4722-4732 (2010), A. Keyvanloo, B. Burke, B. Warkentin, T. Tadic, S. Rathee, C. Kirkby, D. M. Santos, B. G. Fallone, "Skin Dose in Longitudinal and Transverse Linac-MRIs using Monte-Carlo and realistic 3D MRI field models", Medical Physics, 39(10), pp. 6509-6521(2012), and A. Keyvanloo, B. Burke, J. St. Aubin, D. Baillie, K. Wachowicz, B. Warkentin, S. Steciw, and B. G. Fallone, "Minimal skin dose increase in longitudinal rotating biplanar Linac-MR systems: examination of radiation energy and machine dose rate", Physics in Medicine and Biology, 61, pp. 3527-3539 (2016). Alternatively, dose calculations that incorporate the effects of magnetic fields can be calculated using deterministic methods as described by J. St. Aubin, A. Keyvanloo, C. Vassiliev, B. G. Fallone, "A deterministic solution to the first order linear Boltzmann transport equation in the presence of a magnetic field", Medical Physics, 42(2), pp. 780-793 (2015), and J. St. Aubin, A. Keyvanloo, B. G. Fallone, "Discontinuous finite element space-angle treatment of the first order linear Boltzmann transport equation with magnetic fields: application to MRI-guided radiotherapy", Medical Physics, 43(1), pp. 195-204 (2016).

In another embodiment, dose calculations comprises model based systems such as convolution superposition. Such a system allows the patient to be set up on the treatment machine, imaged, planned and treated in a single session.

Figure 7:
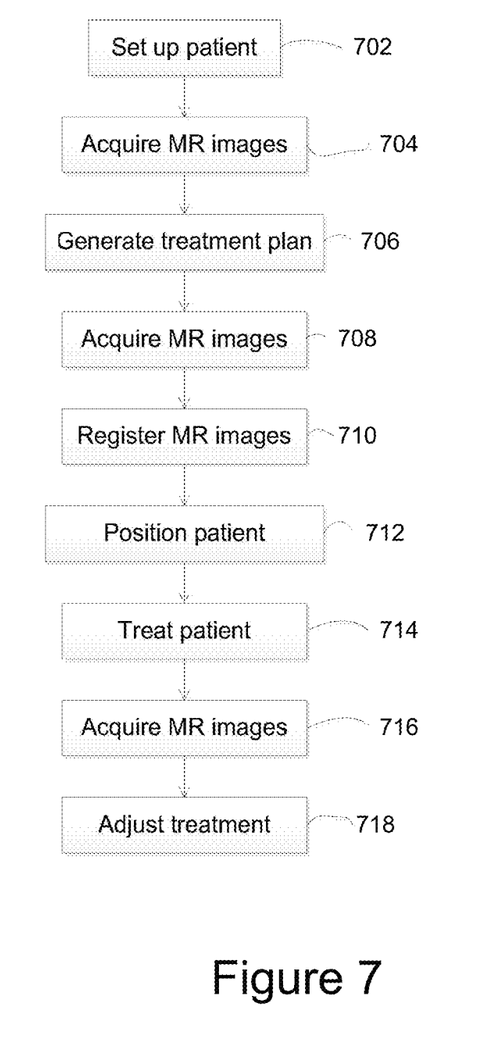
FIG. 7 is a flowchart illustrating the operation of the combined MRI and radiation source.

Referring to FIG. 7, a flowchart illustrating the planning and delivery process is illustrated generally by numeral 700. Initially, the patent P is set up 702 on the patient support system of the MR-SRS system. One or more MR images are acquired 704 and a treatment plan is generated 706. Once the treatment plan has been generated, one or more new MR images are acquired 708 and the MR images are automatically co-registered and aligned 710 to determine if the patient is in the same position as when the plan was generated.

Based on the position of the patient and the treatment plan, the MR-SRS system moves the patient support system to position 712 the patient so that the target is at the isocentre. The patient is treated 714 according to the treatment plan.

While the patent is being treated, further MR images are captured 716 in real time and analysed to determine if there has been any motion of the target position. If motion of the target has been detected, the MR-SRS system adjusts accordingly 718. For example, the MR-SRS system tracks the motion of the target by dynamically modifying the angle of the at least one of the MRI apparatus, the patient support system, and the particle treatment beam. As another example, the beam delivery is held until the target position is reset. Post treatment 3D imaging is acquired for dose summation and adaptation purposes.

Although the MRI imaging is sufficient for the entire planning and delivery process, a clinician may feel that alternate imaging modalities, such as PET, SPECT, and CT for example, are desirable for the treatment planning process. Such imaging may be acquired prior to the treatment plan in generated 706, and incorporated in the treatment plan generation 706 through image fusion techniques.

Figure 8A:
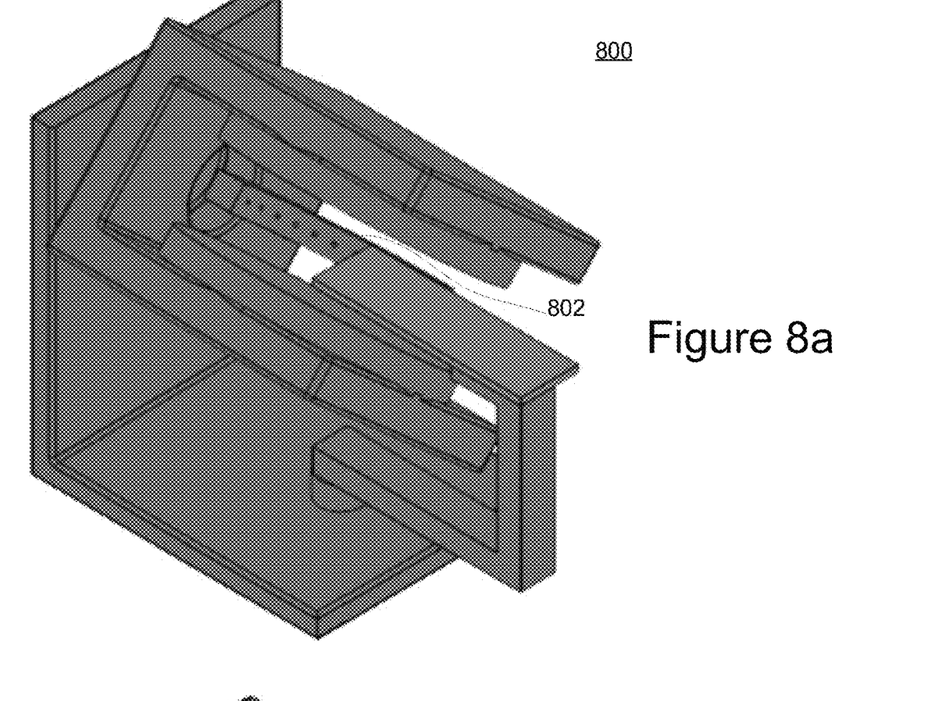
FIGS. 8a, 8b, and 8c illustrate a combined MRI and radiation source in accordance with an alternate embodiment.
Figure 8B:
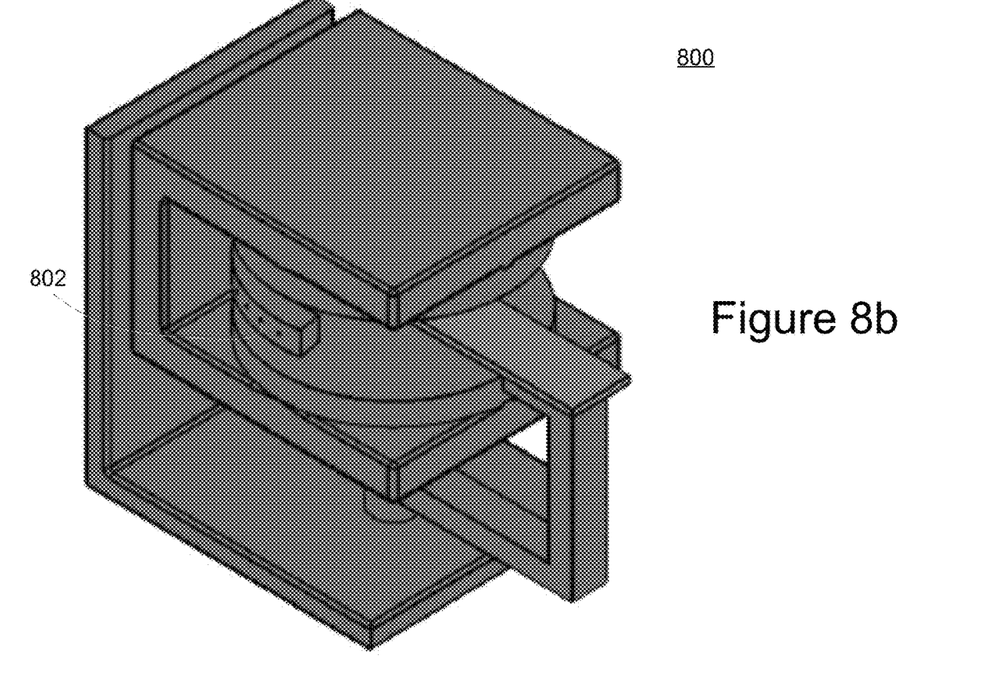
Figure 8C:
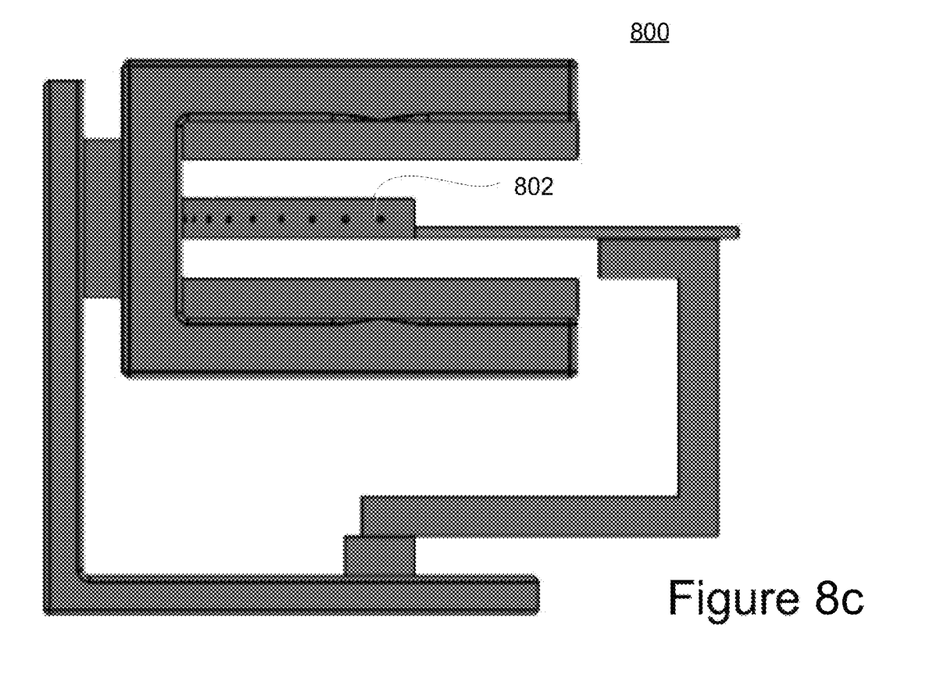

Referring to FIGS. 8a, 8b, and 8c, another embodiment is illustrated generally by numeral 800. In this embodiment, rather than use the accelerator arm 404 and the azimuthal gantry 406 to position the radiation source 112, the MR-SRS system 400 comprises a fixed, arcuate radiation source tray 802. The source tray 802 includes a plurality of radiation sources 112 spaced apart at varying locations in the azimuthal plane. In this embodiment, the source tray 802 is couple to the magnet gantry 122 either directly or indirectly via the perpendicular coupling plate 402. Accordingly, the source tray 802 will be positioned proximal the patient's head when the patient is positioned on the patient support system.

Figure 9:
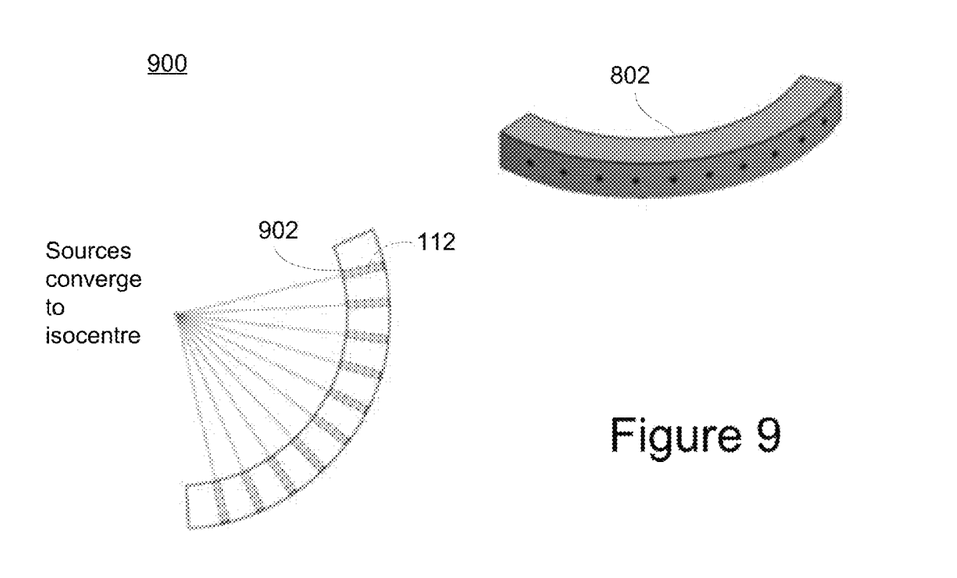
FIG. 9 illustrates an arcuate tray used in the embodiment illustrated in FIGS. 8a, 8b, and 8c.

Referring to FIG. 9, an example of the source tray 802 is illustrated in greater detail. In this example, the source tray 802 comprises 10 radiation sources. Each radiation source (not shown) is a 60Co gamma ray source. Each of the 60Co gamma ray sources are positioned 10 degrees apart. The source tray comprises a plurality of openings 902 that direct the gamma rays from the radiation sources towards the isocentre. A collimating device (not shown) could be used dynamically at each source tray opening to further define the field size from each individual radiation source or block the radiation source entirely, eliminating the gamma ray flux from that radiation source. Thus, the collimating device would be able to control the gammy rays propagating from each of the radiation sources during treatment as determined during treatment planning. As described in other embodiments, the magnet gantry can rotate up to 360 degrees, thus providing radiation delivery over the $2\pi$ steradians or the upper hemisphere.

The source tray 802 and collimator (not shown) will be in close proximity to the magnetic field of the MRI apparatus 114, and as such they should be made of non-magnetic material, such as lead or stainless steel, in order to minimize the effect on the magnetic field homogeneity. Those skilled in the art will also recognize that eddy currents can be generated in the metal of the source tray 802, which could cause image distortions. Standard procedures can be used to minimize eddy currents by using laminated materials or putting insulators between sections of the source tray.

The source tray 802 could house radiation sources separated from 0 degrees (pointed into the top of the head) to 90 degrees (pointed to the side of the head) at 10 degree spacing for a total of 10 sources. However, it would be feasible to extend the source tray 902 beyond 90 degrees to cover as much as 130 degrees which would cover more than the upper hemisphere. If the magnet gantry 122 is rotated continuously, each radiation source in the azimuthal plane would deliver a beam along a conical shaped path.

One skilled in the art will recognize that the source tray 802 could be implemented in an MR-SRS system 400 in which the magnet gantry 122 is positioned at multiple discrete positions (or magnet gantry angles). In such an example, if 10 degree magnet gantry separation is also used, there would be 36 magnet gantry positions with 10 azimuthal radiation source positions giving a total of 360 fixed beam delivery positions, which is adequate to get the extremely sharp dose fall off that is required for stereotactic delivery.

As will be appreciated by a person skilled in the art, alternate source spacing can be used if desired. Additionally, in order to achieve more source positions, the source trays can be stacked in an offset fashion relative to each other to achieve the mechanical space required as long as both sets of source trays are angled such that all sources are still pointed to the isocentre.

Although preferred embodiments of the invention have been described herein, it will be understood by those skilled in the art that variations may be made thereto without departing from the scope of the appended claims.

What is claimed is:

1. A magnetic resonance imaging (MRI) and radiation therapy system, the system comprising:
   a magnet gantry configured to rotate about a magnet gantry axis;
   an MRI apparatus coupled to the magnet gantry;
   a patient support system; and
   a radiation source head coupled to the MRI apparatus via a radiation source arm;
   wherein the radiation source head is configured to emit a treatment beam at varying angles with respect to an azimuthal gantry axis.

2. The system of claim 1, wherein the azimuthal gantry axis is perpendicular to the magnet gantry axis.

3. The system of claim 2, wherein a particle accelerator is mounted on the radiation source arm, and the radiation source arm is rotationally coupled to the MRI apparatus at an azimuthal gantry.

4. The system of claim 1, wherein, the MRI apparatus is a bi-planar MRI apparatus comprising a pair of spaced apart magnetic poles.

5. The system of claim 1, wherein the patient support system is rotationally coupled to a fixed point at a couch gantry.

6. The system of claim 5, wherein the fixed point is a frame of the system or a floor.

7. The system of claim 3, wherein the azimuthal gantry is connect to a magnetic pole of the MRI apparatus.

8. The system of claim 1, wherein the magnet gantry axis is coaxial with a long axis of the patient support system.

9. The system of claim 8, wherein the patient support system is configured to orient the patient in a horizontal position or in a vertical position.

10. The system of claim 1, wherein a degree of rotation about the respective axis of at least one of the MRI apparatus, the patient support system, and the radiation source head is modified dynamically.

11. The system of claim 1, wherein a particle accelerator is located remote from the radiation source arm, the system further comprising:
   a waveguide configured to transport the beam from the particle accelerator to the radiation source head; and
   bending magnets configured to controllably vary an angle at which the beam exits the radiation source head with respect to an azimuthal gantry axis.

12. The system of claim 11, wherein the bending magnets are controllable by altering currents applied to the bending magnets.

13. The system claim 1, wherein the MRI apparatus is a cylindrical magnet.

14. A method for performing stereotactic radiosurgery (SRS) using a magnetic resonance (MR)-SRS system, the method comprising:
   generating a treatment plan in accordance with at least one acquired MR image of a target;
   treating the target using a radiotherapy treatment beam of the MR-SRS system based on the treatment plan, wherein the MR-SRS system comprises a magnet gantry configured to rotate about a magnet gantry axis; an MRI apparatus coupled to the magnet gantry; a patient support system; and a radiation source head coupled to the MRI apparatus via a radiation source arm, wherein the radiation source head is configured to emit the radiotherapy treatment beam at varying angles with respect to an azimuthal gantry axis;
   acquiring further MR images simultaneously to the treating the target to detect motion of the target; and
   modifying the treating the target to correct for the motion of the target.

15. The method of claim 14, wherein the modifying the treating the target comprises dynamically modifying an angle at which the radiotherapy treatment beam is directed to the target.

16. The method of claim 15, wherein the angle at which the radiotherapy treatment beam is directed to the target is modified in at least two orthogonal planes.

17. The method of claim 15, wherein the modifying the treating the target comprises holding application of the radiotherapy treatment beam until a position of the target is reset.

18. A magnetic resonance imaging (MRI) and radiation therapy system, the system comprising:
   a magnet gantry configured to rotate about a magnet gantry axis,
   an MRI apparatus coupled to the magnet gantry;
   a patient support system; and
   an arcuate radiation source tray coupled to the MRI apparatus, the source tray comprising a plurality of spaced apart radiation sources;
   wherein the radiation source tray is configured to emit a treatment beam at varying angles with respect to an azimuthal axis.

19. The system of claim 18, wherein the source tray further comprises a plurality of openings configured to direct radiation from radiation sources to an isocentre.

20. The system of claim 19 further comprising a collimating device configured to selectively control the radiation propagating from each of the openings.

* * * * *